United States Patent [19]

Altman et al.

[11] Patent Number: 4,700,562
[45] Date of Patent: Oct. 20, 1987

[54] METHOD FOR DETERMINING EFFECTIVENESS OF CATALYTIC DEWAXING REACTOR

[75] Inventors: Lawrence J. Altman, Cherry Hill; James B. Milliken, Paulsboro, both of N.J.

[73] Assignee: Mobil Oil Corporation, New York, N.Y.

[21] Appl. No.: 816,939

[22] Filed: Jan. 8, 1986

[51] Int. Cl.$^4$ ............................................. G01N 33/28
[52] U.S. Cl. ............................................. 73/64; 374/45
[58] Field of Search .................... 374/16, 24, 45, 54; 73/64; 436/139, 159

[56] References Cited

U.S. PATENT DOCUMENTS

| | | | |
|---|---|---|---|
| 3,248,928 | 5/1966 | Conklin et al. | 73/64 |
| 3,590,627 | 7/1969 | Campbell | 374/54 |
| 3,668,113 | 6/1972 | Burbidge et al. | 208/97 |
| 3,755,138 | 8/1973 | Chen et al. | 208/33 |
| 3,894,938 | 7/1975 | Gorring et al. | 208/97 |
| 4,137,148 | 1/1979 | Gillespie et al. | 208/87 |
| 4,164,136 | 8/1979 | Wiggins et al. | 73/17 R |
| 4,222,855 | 9/1980 | Pelrine et al. | 208/111 |

*Primary Examiner*—Stewart J. Levy
*Assistant Examiner*—Hezron E. Williams
*Attorney, Agent, or Firm*—A. J. McKillop; M. G. Gilman; V. D. Harrison

[57] ABSTRACT

The pour point of a catalytically dewaxed hydrocarbon oil is determined manually by the ASTM D-97-66 method and also by automatic apparatus such as the Herzog Electronic Pour Point Automatic MC 850 apparatus. A substantial divergence of the two indicates contamination by a waxy hydrocarbon oil such as the feedstock to the dewaxing process.

1 Claim, No Drawings

METHOD FOR DETERMINING EFFECTIVENESS OF CATALYTIC DEWAXING REACTOR

NATURE OF INVENTION

This invention is concerned with the manufacture of high-quality lubricating oils and in particular is concerned with the catalytic dewaxing and hydrotreating of waxy lubricating oils. More specifically, this invention is concerned with a method for determining if channeling of waxy feedstock through the dewaxing catalyst bed is occurring. The method is also useful in detecting fluid leakage in heat exchange between the incoming waxy feedstock (waxy raffinate) and outgoing dewaxed product.

BACKGROUND OF THE INVENTION

The refining of petroleum crude oils to obtain lubricant-stocks is based primarily on a series of steps including distillation, solvent refining and dewaxing.

For the preparation of a high grade distillate lubricating oil stock, the current practice is to vacuum distill an atmospheric tower residuum from an appropriate crude oil as the first step. This step provides one or more raw stocks within the boiling range of about 450° to 1050° F. After preparation of a raw stock of suitable boiling range, it is extracted with a solvent, e.g., furfural, phenol, n-methyl pyrrolidone, sulfolane, or chlorex, which is selective for aromatic hydrocarbons, and which removes undesirable components. The raffinate from solvent refining is then dewaxed, for example, by admixing with a solvent such as a blend of methyl ethyl ketone and toluene. The mixture is chilled to induce crystallization of the paraffin waxes which are then separated from the raffinate. Sufficient quantities of wax are removed to provide the desired pour point for the raffinate.

Other processes such as hydrofinishing or clay percolation may be used if needed to reduce the nitrogen and sulfur content or improve the color of the lubricating oil stock.

In recent years catalytic techniques have become available for dewaxing petroleum stocks. Although some attention has been directed to treating gas oils and manufacturing specialty oils, primary interest has been and is the catalytic dewaxing and subsequent treatment of lube oil stocks. Processes relating to the dewaxing of gas oils and specialty oils are described in U.S. Pat. Nos. 3,894,938 and 4,137,148.

U.S. Pat. No. 3,894,938 discloses a catalytic dewaxing process in which high-pour-point, high-sulfur gas oils having a boiling range of about 400° F. to 900° F. are first contacted, in the presence or absence of added hydrogen, with a ZSM-5 type zeolite hydrodewaxing catalyst which may contain a hydrogenation/dehydrogenation component. The effluent therefrom is subsequently desulfurized and denitrogenated by contacting it with a cobalt-molybdenum-alumina catalyst.

U.S. Pat. No. 4,137,148 discloses a process wherein specialty oils of low pour point and excellent stability are produced from waxy crude distillates having a boiling range of 450° F. to 1050° F. by solvent refining, catalytic dewaxing over a zeolite catalyst such as ZSM-5, and hydrotreating. The catalytic dewaxing reaction produces olefins which would impair properties of the dewaxed oil product if retained. These are saturated by hydrogenation in the hydrotreater, as confirmed by chemical analysis of the hydrotreated product for bromine number. Low bromine numbers are an indication of a satisfactory level of saturation. The hydrotreating step constitutes cascading effluent from the catalytic dewaxing step into a hydrotreating reactor of the type now generally employed for the finishing of lubricating oil stocks. Any of the known hydrotreating catalysts consisting of a hydrogenation component on a non-acidic support can be employed, for example, cobalt-molybdate or nickel-molybdate or molybdenum oxide, on an alumina support. Subsequent to this treatment, the effluent of the hydrotreater is topped by distillation to meet flash and firepoint specifications.

Techniques for dewaxing and subsequent treating of lubricating oil stocks are exemplified in U.S. Pat. Nos. 3,755,138 and 4,222,855.

U.S. Pat. No. 3,755,138 discloses a process wherein a lube oil stock boiling between 650° F. and 1100° F. is subjected to mild solvent dewaxing and subsequently to hydrodewaxing. The hydrodewaxing step constitutes contacting the lube oil stock with a crystalline aluminosilicate of the ZSM-5 type which contains a metal hydrogenating component in the presence of added hydrogen. In U.S. Pat. No. 4,222,855 lube oil stocks boiling between 600° F. and 1050° F. are catalytically dewaxed by contacting them with a crystalline aluminosilicate having particularly characterized pore openings such as ZSM-23 and ZSM-35.

U.S. Pat. No. 3,668,113 discloses a process in which petroleum fractions such as gas oil and wax distillate fractions are first passed over a catalyst comprising a crystalline mordenite of reduced alkali metal content and a metal hydrogenating component to remove wax. The reaction product is then passed over a catalyst comprising a refractory inorganic oxide support and a hydrogenating component selected from metals and compounds thereof of Groups VI and VIII of the Periodic Table to remove sulfur.

A currently preferred process is one wherein the actual dewaxing is accomplished in a first reactor using a zeolite catalyst such as the ZSM-5 zeolite and then hydrofinishing the dewaxed effluent in a second reactor in order to reduce olefinic compounds produced in the first reactor. The hydrofinishing step produces a base stock having an acceptable oxidative stability.

A problem associated with the dewaxing step in the first reactor is that channeling or bypassing might occur in which a small portion of the waxy raffinate from the solvent refining step flows almost directly through the reactor bed with minimal contact with the catalyst. Consequently, little if any, dewaxing occurs in this portion of the raffinate. The resulting product may not meet critical performance tests even though pour point or cloud point specifications are met. Another possible problem can occur in the heat exchange system. Ordinarily the system is designed to transfer heat from the heated dewaxed product stream downstream to the cooler incoming waxy raffinate upstream where the pressure is higher. If any leaks across the physical barriers separating the two systems occur, the product effluent (the dewaxed product) will be contaminated and be of unacceptable specifications.

OBJECTS OF THE INVENTION

A primary object of this invention is to provide a method of determining when channeling or bypassing is occurring in a reactor bed, such as that used in catalytic dewaxing, or when heat exchanger leaks are occurring.

Other objects of the invention will become apparent from the disclosure which follows.

SUMMARY OF THE INVENTION

We have discovered that the presence of wax in supposedly catalytically dewaxed raffinate can be detected by determining the pour point of a sample by each of two separate methods and then comparing the pour points. A substantial difference in the determined pour points is indicative of the presence of wax impurities. The methods are of the type which, if used on a uncontaminated sample, would yield nearly identical pour point readings. The tests are:

1. The ASTM Standard Test Method for determining the pour point of petroleum oils designed as ASTM test D-97-66 (reapproved 1978) and
2. The pour point determined using a shear pour point device such as that described in U.S. Pat. No. 4,164,136 to Wiggins et al.

DESCRIPTION OF THE INVENTION

As noted previously, the method of this invention is based on two independent determinations of pour point. The first of these tests is a manual test and is best described as that test corresponding to the ASTM test designated D-97-66 (reapproved 1978) I.P. designation: 15/67 (75). This test is described in Volume 5.01 of the 1985 Annual Book of ASTM Standards published by the American Society of Testing Materials, Philadelphia, PA, Publication Code No. (PCN:01-050185-12). That test is described on pages 85 through 88 of this publication. Those pages are incorporated herein by reference. This test can be summarized as one wherein the sample to be tested for pour point is placed in a tube and is successively cooled and after routine thermo-equilibrium is tilted to determine if the sample will still flow. The temperature at which no flow of oil is discernible is adjusted and called the pour point for that particular sample. Those skilled in the art are well acquainted with the techniques for conducting this test.

The second test is based on positioning a probe so that its lower end extends within a sample of the oil being tested. The sample is cooled slowly while an intermittent torque is placed on the probe inserted in the sample. The point at which the probe's ability to rotate in the oil medium is lessened or becomes non-existent is known as the pour point of the sample. Apparatus for this technique is described in U.S. Pat. No. 4,164,136 which is incorporated herein by reference. This type of apparatus is also embodied in the Herzog Electronic Pour Point-Automatic MC 850 model. This apparatus is manufactured by the Walter Herzog GmbH and distributed in the U.S. by UIC, Inc., Joliet, Ill.

As indicated previously, this latter apparatus operates on the principle that if a liquid surrounding the probe is cooled as a rotational force is applied to the liquid body, that the probe eventually will rotate when the pour point of the liquid has been reached. This occurs because as the sample congeals it tends to grab onto the probe as the pour point is reached. If pour point determinations are made on a pure sample, i.e., a sample uncontaminated by waxy materials, the two pour points by the ASTM method and the Herzog method will be essentially the same. We have discovered, however, that if the pour points are run on samples containing waxy raffinate from the original reactor, there will be a substantial difference in pour points which increases as the amount of raffinate or other waxy impurity increases. We have made a number of tests showing what happens when these samples are tested.

EXAMPLES

The following table presents summaries of tests in which portions of dewaxed oil was mixed with the undewaxed or waxy-containing raffinate in increasing proportions. Tests were then run using each of the previously identified tests to determine pour point. From the resulting data it is readily apparent that even a minor increase in the concentration of wax in the treated oil results in a wide divergence from the pour point of the pure uncontaminated sample. The pour point determinations were made using the ASTM D-97-66 test and the Herzog Electronic Pour Point Automatic MC850 model distributed by the UIC Corporation of Joliet, Ill.

TABLE

Comparison of Pour Points of Various Concentrations of Waxy Raffinate in Dewaxed Oil as Determined By the ASTM D97 Method and by the Herzog Apparatus

| Run No. | Concentration of High Pour Point (Waxy Raffinate) Component, Percent | Pour Point °F. by D97 | Pour Point °F. by Herzog |
|---|---|---|---|
| \multicolumn{4}{c}{73° F. Pour Point Light Neutral Oil Added to −10° F. Pour Point Dewaxed Light Neutral Oil} |
| 1 | 0 | −10 | −13 |
| 2 | 1 | −10 | −13 |
| 3 | 2 | −5 | −10 |
| 4 | 4 | 15 | −9 |
| 5 | 8 | 25 | −3 |
| 6 | 12 | 40 | 4 |
| 7 | 16 | 45 | 10 |
| \multicolumn{4}{c}{Light Neutral Waxy Raffinate Added to −20° F. Pour Point Dewaxed Light Neutral Oil} |
| 8 | 0 | −20 | −14 |
| 9 | 1 | −15 | −18 |
| 10 | 2 | 5 | −13 |
| 11 | 4 | 20 | −6 |
| 12 | 8 | 40 | 2 |
| 13 | 12 | 60 | 18 |
| 14 | 16 | 60 | 21 |
| \multicolumn{4}{c}{Light Neutral Waxy Raffinate Oil Added to 0° F. Pour Point Dewaxed Light Neutral Oil} |
| 15 | 0 | 0 | −2 |
| 16 | 1 | 10 | 0 |
| 17 | 2 | 20 | 2 |
| 18 | 4 | 35 | 4 |
| 19 | 8 | 55 | 19 |
| 20 | 12 | 60 | 26 |
| \multicolumn{4}{c}{73° F. Pour Point Light Neutral Oil Added to 15° F. Pour Point Dewaxed Light Neutral Oil} |
| 21 | 0 | 15 | 12 |
| 22 | 1 | 15 | 12 |
| 23 | 2 | 15 | −8 |
| 24 | 4 | 15 | 12 |
| 25 | 8 | 35 | 18 |
| 26 | 12 | 45 | 20 |
| 27 | 16 | 55 | 28 |
| \multicolumn{4}{c}{Light Neutral Waxy Raffinate Added to 22° F. Pour Point Dewaxed Light Neutral Oil} |
| 28 | 0 | 20 | 9 |
| 29 | 1 | 25 | 9 |
| 30 | 2 | 35 | 11 |
| 31 | 4 | 35 | 14 |
| 32 | 8 | 55 | 23 |
| 33 | 12 | 55 | 31 |
| 34 | 16 | 65 | 37 |
| \multicolumn{4}{c}{Heavy Neutral Waxy Raffinate Added to 15° F. Pour Point Dewaxed Heavy Neutral Oil} |
| 35 | 0 | 15,10 | 9 |
| 36 | 1 | 20,10 | 9 |
| 37 | 2 | 15,10 | 10 |
| 38 | 4 | 25 | 12 |
| 39 | 8 | 50 | 16 |
| 40 | 12 | 80 | 26 |

TABLE-continued

Comparison of Pour Points of Various Concentrations of Waxy Raffinate in Dewaxed Oil as Determined By the ASTM D97 Method and by the Herzog Apparatus

| Run No. | Concentration of High Pour Point (Waxy Raffinate) Component, Percent | Pour Point °F. by D97 | Pour Point °F. by Herzog |
| --- | --- | --- | --- |
| 41 | 16 | 80 | 30 |

What is claimed is:

1. A method for determining the presence of waxy impurities in a catalytically dewaxed hydrocarbon oil comprising:
    (a) determining the pour point temperature of a first sample of said hydrocarbon oil using a first method;
    (b) determining the pour point temperature of a second sample of said hydrocarbon oil using a second method which would yield approximately the same pour point as that of the first method;
    (c) comparing the pour point temperature determined by said first method with the pour point temperature determined by said second method; and
    (d) determining the presence of said waxy impurities by the difference in value obtained in step (c).

* * * * *